United States Patent
Sumiyoshi et al.

(10) Patent No.: US 9,889,475 B2
(45) Date of Patent: Feb. 13, 2018

(54) ADHESIVE MATERIAL FOR USE IN RESIDUE CONFIRMATION, AND METHOD FOR CONFIRMATION OF RESIDUE REMAINING ON OBJECT TO BE CLEANED AFTER CLEANING USING THE SAME

(71) Applicant: SUGINO MACHINE LIMITED, Uozu, Toyama Prefecture (JP)

(72) Inventors: Toru Sumiyoshi, Shimoniikawa-gun (JP); Toyoaki Mitsue, Toyama (JP); Yuichi Motoshima, Kurobe (JP)

(73) Assignee: SUGINO MACHINE LIMITED, Uozu Toyama Prefecture (JP)

( * ) Notice: Subject to any disclaimer, the term of this patent is extended or adjusted under 35 U.S.C. 154(b) by 624 days.

(21) Appl. No.: 14/496,550

(22) Filed: Sep. 25, 2014

(65) Prior Publication Data
US 2015/0107624 A1    Apr. 23, 2015

(30) Foreign Application Priority Data
Oct. 18, 2013   (JP) ................................. 2013-216994

(51) Int. Cl.
| | |
|---|---|
| B08B 3/02 | (2006.01) |
| B08B 7/04 | (2006.01) |
| C09K 11/00 | (2006.01) |
| G01N 21/64 | (2006.01) |
| B08B 13/00 | (2006.01) |
| B23Q 11/00 | (2006.01) |

(52) U.S. Cl.
CPC .................. *B08B 3/02* (2013.01); *B08B 7/04* (2013.01); *B08B 13/00* (2013.01); *B23Q 11/0075* (2013.01); *C09K 11/00* (2013.01); *G01N 21/64* (2013.01); *G01N 2021/6495* (2013.01)

(58) Field of Classification Search
CPC .. B08B 13/00; B08B 7/00; B08B 7/04; B08B 3/02; C09K 11/00; B23Q 11/0075; G01N 21/64; G01N 2021/6495; Y02P 70/71
See application file for complete search history.

(56) References Cited

U.S. PATENT DOCUMENTS

| | | | |
|---|---|---|---|
| 6,476,385 B1 * | 11/2002 | Albert .................... | G01N 21/91 |
| | | | 250/301 |
| 2006/0223731 A1 | 10/2006 | Carling | |
| 2016/0002525 A1 * | 1/2016 | Wegner ............... | C09K 11/025 |
| | | | 250/473.1 |

FOREIGN PATENT DOCUMENTS

| | | |
|---|---|---|
| CH | 686852 A5 | 7/1996 |
| DE | 19649925 A1 | 6/1998 |
| EP | 2392906 A1 | 12/2011 |
| JP | A-2011-206619 | 10/2011 |

OTHER PUBLICATIONS

Mar. 6, 2015 Extended European Search Report issued in European Patent Application No. EP 14 18 9188.7.

* cited by examiner

*Primary Examiner* — Saeed T Chaudhry
(74) *Attorney, Agent, or Firm* — Oliff PLC

(57) ABSTRACT

A residue remaining on an object to be cleaned after cleaning is easily detected and observed on the object. Adhesive materials for use in residue confirmation, which are applied in advance to an object to be cleaned for confirmation of a residue remaining on the object after cleaning, are formed by coloring chips produced during cutting work. The adhesive materials are preferably formed by coating and coloring the chips with paint, the paint emitting visible light in an excited state.

4 Claims, 3 Drawing Sheets

ADHESIVE MATERIAL FOR USE IN RESIDUE CONFIRMATION, AND METHOD FOR CONFIRMATION OF RESIDUE REMAINING ON OBJECT TO BE CLEANED AFTER CLEANING USING THE SAME

BACKGROUND

1. Field of the Invention

The present invention relates to an adhesive material for use in residue confirmation, which is applied in advance to an object to be cleaned for confirmation of a residue remaining on the object after cleaning, and a method for confirmation of a residue remaining on the object after cleaning using the adhesive material, in cleaning of objects to be cleaned such as machine parts.

2. Description of the Related Art

Examples of the machine parts include parts cut from an extruded material and parts with a material formed by casting as a starting material. Machine parts are generally manufactured by subjecting the starting material to milling, drilling, tapping, polishing or other machining, and further surface treatment. Cleaning of the machine parts is performed while they are being machined, or before or after they are machined, or after the surface treatment. The cleaning is aimed at removing a casting mold release agent or sand mold adhering to the starting material, chips produced by machining, foreign particles caused by conveyance of an intermediate workpiece in process of machining, foreign particles deposited by surface treatment, etc. from an object (workpiece) to be machined or treated.

The workpiece after machining, which is to be cleaned by a cleaning apparatus, is referred to as the object to be cleaned, and sometimes simply as the object. The workpiece with chips thereon, as the object to be cleaned, is conveyed to the cleaning apparatus.

Most of the dirt adhering to the object to be cleaned, that is, the residue remaining on the object to be cleaned, is chips produced during cutting work of machine parts. The shape of the chips changes depending on the cutting methods and conditions, and includes a helical shape, thin sheet rectangular piece, spiral, disc or other irregular shapes. These chips may fall into a recess, screw hole, water hole, crossing hole, etc. provided in a workpiece when the workpiece is machined. Furthermore, because the chips have irregular shapes, edges of the chips pierce the object to be cleaned or get caught in a hollow portion in the object to be cleaned, so that the chips and the object to be cleaned may be joined together.

Examples of the cleaning apparatus include a spray cleaning machine. The spray cleaning machine is configured such that an object to be cleaned is put into the cleaning machine, and then cleaning liquid increased in pressure by a high-pressure pump is jetted from a nozzle to thereby wash the object.

Within the spray cleaning machine, the chips fall off the object under the dynamic pressure of the jet jetted from the nozzle. Then the chips leave the object along with the flow produced by the jet jetted from the nozzle. However, the chips joined to the object are hard to remove with a jet of the sprayed cleaning liquid.

As a related-art technology, a method is known (see, for example, Japanese Published Unexamined Patent Application No. 2011-206619), in which cleaning water used for cleaning components is filtered by a filter and dust accumulated on the filter is directly observed with a microscope or the like to evaluate the cleanliness of various components, such as machine parts or optical components, after cleaning.

The Japanese Published Unexamined Patent Application No. 2011-206619 discloses the technology for counting dust particles captured by the filter or observing the shapes of the particles with an optical microscope.

Furthermore, the cleaning capacity evaluation can be also conducted by causing the residue adhering to the object after cleaning to collect on the filter and measuring the total mass and size.

In this case, firstly, the mass of the filter in a dry state is measured. The object is left at rest on a clean sink, and then clear liquid is poured on the object. The poured liquid is collected, and filtered by the filter to collect a residue. The filter is dried, and the mass of the filter is measured again. The difference in the mass of the filter before and after filtration is expressed as the amount of residue. The smaller the amount of residue is, the higher the cleaning capacity evaluation is.

Meanwhile, in the spray cleaning machine, in order to improve the cleaning capacity, it is important that the jet jetted from the nozzle enters the area on the object where dirt is stuck.

Therefore, if the area on the object where chips remain can be specified, rather than merely detecting the amount of the residue remaining on the object after cleaning, the nozzle can be positioned or the moving path of the nozzle can be changed so that a water jet strongly hits a specified position. Furthermore, the change in the position or moving path of the nozzle allows an improvement in cleaning capacity of the cleaning apparatus.

While the above is a description with the spray cleaning machine as an example, specifying the area where chips remain is essential for improving the cleaning capacity even in other cleaning apparatuses, such as a cleaning apparatus in which the object to be cleaned is placed in a water jet and cleaned by devising the flow structure of the water jet. In other words, specifying the area of the object after cleaning where chips remain is useful for improving the cleaning capacity regardless of the cleaning method.

However, in the method in which the cleaning liquid used for cleaning the object to be cleaned is filtered by the filter to thereby collect and evaluate the residue adhering to the object, the area on the object where chips remain cannot be specified.

In order to specify the area of an object to be cleaned where chips remain, therefore, there is a possible approach, in which the object with chips intentionally applied thereto is put into a spray cleaning machine to confirm which area of the object after cleaning the chips remain in. The chips used here are chips produced in an actual process line or chips of the same material as the chips produced in an actual process line. This is because the rigidity and shapes of the chips vary depending on the cutting conditions and the joining forms of the chips to the object change. For this reason, the chips to be applied to the object are preferably of the same material as the object.

In this case, because the chips and the object to be cleaned are of the same material, the surface colors of the chips and the object to be cleaned are the same or similar. Furthermore, because the object to be cleaned is manufactured by machining an extrusion or casting as a starting material, the surface of the object includes a casting surface, extrusion surface, and machined surface. Regardless of the casting method, generally, the casting surface has very fine uneven shapes, and when it is visually observed, shades in a fine pattern on the uneven surface caused by external light are observed.

Furthermore, the pattern made by a rotary cutting tool in contact with the workpiece is observed on the machined surface. Also, if the machined surface has a casting defect, shades are made on the defective places of the machined surface. In this manner, the surface of the machine parts has generally almost the same color and various fine shades.

To specify the area where chips remain after cleaning, it is necessary to find the chips of the same color as the object while lying on the surface of the object which is wide and has various shades. However, it is very hard to distinguish between the chips and the shades on the object. Therefore, there still remains the problem that the area on the object after cleaning where chips remain cannot be specified.

SUMMARY

Accordingly, an object of the present invention is to easily find and confirm a residue on an object to be cleaned after cleaning.

In order to achieve the above-mentioned object, a first aspect of the present invention provides an adhesive material for use in residue confirmation which is applied in advance to an object to be cleaned for confirmation of a residue remaining on the object after cleaning. The adhesive material is formed by coloring chips produced during cutting work.

According to the first aspect of the present invention, the adhesive material for use in residue confirmation is formed by coloring the chips. Thus, the surface colors of the adhesive material for use in residue confirmation and the object to be cleaned can be made different and clearly distinguished from each other, so that the adhesion state and residual state of the adhesive material for use in residue confirmation can be easily visually confirmed.

That is, it is possible to provide the adhesive material for use in residue confirmation which allows the residue remaining on the object after cleaning to be easily found and confirmed on the object.

Furthermore, the chips are used as the dirt adhering to the object after cleaning, that is, the adhesive material for use in residue confirmation applied in advance for confirming the state of the residue remaining on the object. Therefore, the adhesion state similar to the adhesion state of dirt to the object to be cleaned after actual machining can be properly reproduced by using the adhesive material for use in residue confirmation, and the cleaning capacity evaluation can be conducted with high accuracy.

It should be noted that in this specification, the "coloring" includes not only adding a color different from a basis material color under indoor light or sunlight, but also adding a color which can be expected to be distinguished from the periphery by emitting light when necessary although colorless and transparent under indoor light or sunlight.

Furthermore, preferably, the chips are coated with paint, the paint emitting visible light in an excited state.

With this constitution, because the chips colored by being coated with paint emit visible light when energized and excited, the adhesive material for use in residue confirmation can be easily found.

Moreover, preferably, the paint is fluorescent paint.

With this constitution, the chips colored by being coated with fluorescent paint emits fluorescence by irradiating the object with ultraviolet or near-ultraviolet light under the condition in which external light is blocked. Thus, the area where the adhesive material for use in residue confirmation remains can be easily found and specified.

Further, preferably, the chips are colored in a plurality of colors according to sizes of the chips.

With this constitution, on the object, the sizes and positions of the colored chips serving as the adhesive material for use in residue confirmation can be grasped at the same time.

Furthermore, preferably, the chips are made of a material of the same kind as that of the object.

With this constitution, the rigidity and shapes of the chips serving as the adhesive material for use in residue confirmation are close to those produced during actual cutting work. Therefore, the adhesion state similar to the adhesion state of dirt to the object to be cleaned after actual machining can be more properly reproduced by using the adhesive material for use in residue confirmation.

Additionally, preferably, the chips are extracted from a process line for cutting work the object before cleaning.

With this constitution, the rigidity and shapes of the chips serving as the adhesive material for use in residue confirmation are the same as those produced during actual machining. Therefore, the adhesion state similar to the adhesion state of dirt to the object to be cleaned after actual machining can be further properly reproduced by using the adhesive material for use in residue confirmation.

A second aspect of the present invention provides a method for confirmation of a residue remaining on an object to be cleaned after cleaning. The method includes the steps of: applying to the object the adhesive material for use in residue confirmation formed in such a manner that the chips produced during cutting work are colored by being coated with paint, the paint emitting visible light in an excited state; cleaning the object with the adhesive material applied thereto; and energizing the object after cleaning for excitation.

According to the second aspect of the present invention, it is possible to detect only the chips colored by being coated with the paint which is excited by receiving energy. Thus, the area where the adhesive material for use in residue confirmation remains can be easily found and specified.

That is, it is possible to provide the method for confirmation of a residue remaining on the object after cleaning, which allows the residue remaining on the object after cleaning to be easily found and confirmed on the object.

According to the aspects of the present invention, the residue remaining on the object after cleaning can be easily found and confirmed on the object.

It is therefore possible to generally improve the cleaning capacity by focusing on cleaning the area of the object after cleaning where the residue remains.

BRIEF DESCRIPTION OF THE DRAWINGS

Embodiments of the present invention will be described in detail based on the following drawings, in which:

FIGS. 3A and 3B are photographs, substituted for the drawings, showing the state of the object after cleaning the object with the adhesive material for use in residue confirmation applied thereto, the adhesive material being formed by coating and coloring chips with fluorescent paint, wherein FIG. 3A is a photograph, substituted for the drawing, of the object after cleaning, taken under ultraviolet light in a darkroom, and FIG. 3B is a photograph, substituted for the drawing, of the same portion of the same object as FIG. 3A, taken under indoor light.

DETAILED DESCRIPTION

Figure 1:
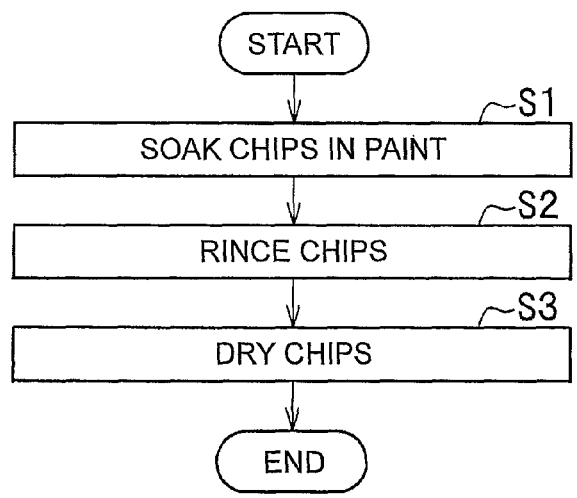
FIG. 1 is a flowchart showing a method for preparing an adhesive material for use in residue confirmation.

An embodiment of the present invention will be described in detail with reference to the accompanying drawings as necessary.

[Adhesive Material for Use in Residue Confirmation]

Firstly, an adhesive material for use in residue confirmation according to an embodiment of the present invention will be described. The adhesive material for use in residue confirmation is applied in advance to an object to be cleaned for confirmation of a residue remaining on the object after cleaning. The adhesive material for use in residue confirmation according to this embodiment is formed by coloring chips produced during cutting work.

The chips used here as the adhesive material for use in residue confirmation are of the same material as the object to be cleaned. However, the materials do not need to be exactly the same.

For example, if the object to be cleaned is made of cast iron, the chips of a material in the same group as cast iron are preferably used. In the same manner, if the material of the object to be cleaned is aluminum alloy, the chips made of alloy in the same group as aluminum alloy are preferably used.

Furthermore, the chips extracted from a process before cleaning in an actual process line are preferably used and colored so that the adhesion state of the chips becomes the same as the adhesion state of chips to an actual object to be cleaned. However, if it is difficult to obtain chips in an actual process line, the chips prepared on the assumption of the existence of a processing machine used in an actual process line may be colored. That is, the cutting work for producing the chips serving as the adhesive material for use in residue confirmation is preferably performed under conditions (including types of processing machines or tools and cutting speed) equivalent to those of a main cutting work to be applied to the object before cleaning.

The chips as a material are colored by soaking them in paints, dyes, chemicals, etc. or spraying paint. The chips need only be colored in a different color from a ground color (basis material color) thereof, preferably in an attention-getting color such as red or yellow.

Moreover, the chips are preferably colored with fluorescent paint, which emits fluorescence when exposed to ultraviolet light. Here, the fluorescent paint includes the paint having a fluorescent material, which emits light in a visible light region by absorbing the ultraviolet or near-ultraviolet light although colorless and transparent under indoor light or sunlight. Alternatively, the chips may be colored with the so-called luminous paint, which is subjected to visible light and emits phosphorescence with the energy of the visible light.

It should be noted that if the material of the chips is aluminum alloy, the chips can be colored yellow by soaking them in hexavalent chromium. Furthermore, if the material of the chips is steel, in place of paint, the chips can be colored greenish yellow by soaking them in iron oxalate; green by soaking them in iron arsenate; green by soaking them in iron selenite; and blue by soaking them in sodium hyposulfite. If the material of the chips is copper, the chips are soaked, for example, in dilute nitric acid and dried to thereby produce green rust of blue-green basic copper nitrate. In addition to these, the metal surfaces of the chips can be colored in various colors by soaking them in chemicals or the like.

[Method for Confirmation of Residue Remaining on Object to be Cleaned after Cleaning]

Next, a method for confirmation of a residue on an object to be cleaned after cleaning using the adhesive material for use in residue confirmation will be described, the adhesive material being formed by coloring chips produced during cutting work as described above.

An operator applies the adhesive material for use in residue confirmation to an object to be cleaned. Here, the object to be cleaned may include a partially-processed workpiece. The adhesive material for use in residue confirmation is applied to the entire object to be cleaned. The amount of the adhesive material for use in residue confirmation to be applied to the object to be cleaned is determined as appropriate in accordance with the cleaning process or conditions.

The object to be cleaned with the adhesive material for use in residue confirmation applied thereto is put into a cleaning machine. The cleaning machine cleans the object to remove the adhesive material for use in residue confirmation applied to the object. After the end of the cleaning, the object is taken out of the cleaning machine. At this time, the adhesive material for use in residue confirmation which is not removed by the cleaning machine adheres to and remains on the object as a residue after cleaning.

Then the operator exposes the object after cleaning to a light source to confirm the position and size of the adhesive material for use in residue confirmation remaining.

Here, the adhesive material for use in residue confirmation according to this embodiment is formed by coloring the chips produced during cutting work.

Thus, the surface colors of the adhesive material for use in residue confirmation and the object to be cleaned can be made different and clearly distinguished from each other, so that the adhesion state and residual state of the adhesive material for use in residue confirmation can be easily visually confirmed. That is, the residue remaining on the object after cleaning can be easily found and confirmed on the object. It is therefore possible to generally improve the cleaning capacity by focusing on cleaning the area of the object after cleaning where a lot of the residue remains.

Here, if the chips serving as the adhesive material for use in residue confirmation are coated and colored with the paint which emits visible light while being excited by receiving energy, the adhesive material for use in residue confirmation which emits visible light in the room where external light is blocked can be more clearly confirmed on the object after cleaning than the chips colored in the attention-getting color. Therefore, the adhesive material for use in residue confirmation which remains on the object can be easily found.

For example, if the adhesive material for use in residue confirmation is the chips coated and colored with fluorescent paint, the fluorescent paint is excited to emit fluorescence as visible light by irradiating the object with ultraviolet light in the so-called darkroom where external light is blocked. In this case, because there is nothing which emits visible light, except the adhesive material for use in residue confirmation, the position where the adhesive material for use in residue confirmation adheres can be easily confirmed.

Furthermore, if the adhesive material for use in residue confirmation is the chips coated and colored with luminous paint, the luminous paint emits phosphorescence as visible light when the object is irradiated with visible light in a darkroom and then the visible light is cut off. Thus, the position where the adhesive material for use in residue confirmation adheres can be easily confirmed.

In the case of using the chips coated with fluorescent paint or luminous paint as the adhesive material for use in residue confirmation, the sizes and shapes of the colored chips serving as the adhesive material for use in residue confirmation can be measured and recorded by marking in a darkroom the position where the adhesive material for use in residue confirmation adheres, and then observing the adhesive material existing in the marked position with a magnifying glass under indoor light.

Also, in this embodiment, the chips produced during cutting work are used as the dirt adhering to the object after cleaning, that is, the adhesive material for use in residue confirmation applied in advance for confirming the state of a residue remaining on the object. Therefore, the colored chips serving as the adhesive material for use in residue confirmation have sharp edges and have appropriate rigidity, elasticity, and shapes, thereby causing the chips to engage in grooves, recesses, machine elements, etc. of the object to be cleaned and hardly fall off in the same manner as chips as a residue remaining after actual machining. Therefore, the adhesion state similar to the adhesion state of dirt to the object to be cleaned after actual machining can be properly reproduced by using the adhesive material for use in residue confirmation, and the cleaning capacity evaluation can be conducted with high accuracy.

Here, if the material of the chips used as the adhesive material for use in residue confirmation is the same kind as that of the object to be cleaned, the rigidity and shapes of the chips used as the adhesive material for use in residue confirmation are close to those produced during actual cutting work. In this case, the adhesion state similar to the adhesion state of dirt to the object to be cleaned after actual machining can be more properly reproduced by using the adhesive material for use in residue confirmation.

Moreover, if the chips used as the adhesive material for use in residue confirmation are extracted from a process line for cutting work the object before cleaning, the rigidity and shapes of the chips used as the adhesive material for use in residue confirmation are the same as those produced during actual cutting work. In this case, the adhesion state similar to the adhesion state of dirt to the object to be cleaned after actual machining can be further properly reproduced by using the adhesive material for use in residue confirmation.

It should be noted that the chips serving as the adhesive material for use in residue confirmation may be colored in a plurality of different colors according to the sizes of the chips. Here, for example, the maximum length (hereinafter also referred to as "long side") between arbitrary two points of the chip in plan view can be used as the chip size. With this constitution, the sizes and positions of the colored chips serving as the adhesive material for use in residue confirmation can be grasped on the object at the same time. For example, the chips serving as the adhesive material for use in residue confirmation are sifted and preliminarily divided into a plurality of size groups so that the chips can be coated with fluorescent paints emitting different fluorescent colors according to the sizes of the chips. Thus, the adhesive material for use in residue confirmation having fluorescent colors which are different for each chip size can be obtained. If this adhesive material is mixed and applied to the object to be cleaned for cleaning, the size groups and positions of the chips can be grasped at the same time by irradiating the object after cleaning with ultraviolet light.

Example

Next, an example of the present invention will be described. However, the technical scope of the present invention is not limited to the following example.

Here, an example of the cleaning evaluation will be shown below. The cleaning evaluation was conducted by using water-soluble fluorescent paint including a fluorescent material to form an adhesive material for use in residue confirmation with aluminum-alloy chips colored by soaking them in the fluorescent paint, and applying the adhesive material for use in residue confirmation to an object to be cleaned made of aluminum alloy, and then cleaning the object.

Referring to FIG. 1, a method for preparing an adhesive material for use in residue confirmation will be described.

Products called "KEIKO CHECK GW-U" manufactured by TASETO CO., LTD. were used as water-soluble fluorescent paint.

Firstly, chips obtained by milling aluminum alloy were soaked in this water-soluble fluorescent paint for a minute (S1).

Subsequently, the chips were extracted from the fluorescent paint, put into a container, and rinsed with tap water. Rinsing was performed by repeating three times the process of filling the container containing the chips with tap water, stirring and then draining the tap water (S2).

Then the chips after rinsing were put into a dryer with a heater and dried by being held at 100° C. for 15 minutes (S3). In this manner, the adhesive material for use in residue confirmation formed by coloring the chips was obtained.

It should be noted that the rinsing process (S2), which is performed for the purpose of preventing the plurality of chips from sticking to each other due to the paint, can be eliminated. Furthermore, the method for coating chips may include spraying paint on the chips in place of soaking the chips in paint. Of course, in the case of using an oil paint, rinsing is performed with an organic solvent.

Also, in this example, the chips were colored with the fluorescent paint including a fluorescent material which emits a fluorescent color. However, an attention-getting color paint including no fluorescent material may be used. If it is difficult to prepare the so-called darkroom where surrounding external light is blocked for inspection, the chips colored in an attention-getting color may be used as a simple method.

Next, referring to FIG. 2, a method for confirmation of a residue remaining on an object to be cleaned after cleaning using the chips colored with fluorescent paint as the adhesive material for use in residue confirmation will be described.

Figure 2:
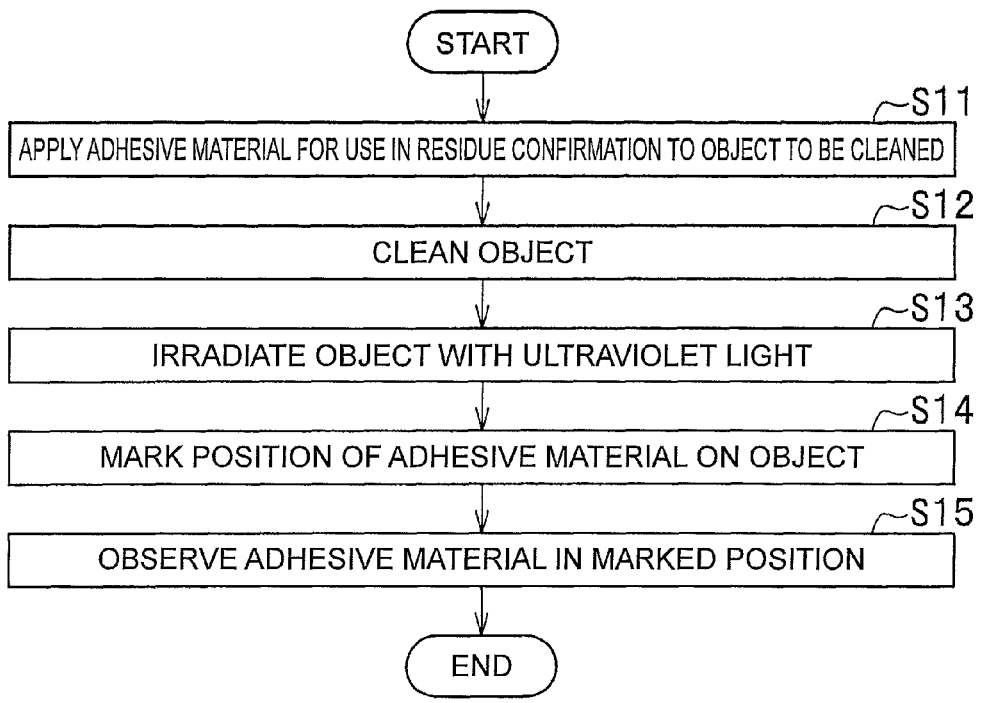
FIG. 2 is a flowchart showing a method for confirmation of a residue remaining on an object to be cleaned after cleaning, using chips colored with fluorescent paint as the adhesive material for use in residue confirmation.

The method for confirmation of a residue remaining on an object to be cleaned after cleaning as shown in FIG. 2 includes the steps of: applying an adhesive material for use in residue confirmation, which is formed by coating and coloring the chips produced during cutting work with fluorescent paint, to an object to be cleaned (S11); cleaning the object with the adhesive material for use in residue confirmation applied thereto (S12); and irradiating the object after cleaning with ultraviolet light for excitation (S13). Then the position on the object where the colored chips used as the adhesive material for use in residue confirmation remain and the colored chips themselves remaining are confirmed.

More specifically, firstly, an operator wears gloves on both hands and sprinkles the adhesive material for use in residue confirmation, which is formed by coating and coloring the chips with the fluorescent paint including a fluorescent material, on the object to be cleaned to make it adhere to the object to be cleaned (S11). At this time, preferably, the adhesive material for use in residue confirmation is mixed with, for example, a machine coolant in a preceding process of the cleaning process. With the coolant, its surface tension brings an improvement in the adhesiveness of chips to the surface of the object to be cleaned, thereby allowing an increase in the amount of adhesion of the adhesive material for use in residue confirmation to the object to be cleaned. Subsequently, the object to be cleaned with the adhesive material for use in residue confirmation applied thereto is put into a cleaning machine to be cleaned (S12). After the completion of the cleaning, the object is taken out.

It should be noted that although it is not always necessary to wear gloves, the gloves are preferably used for protecting operator's fingers because the chips serving as the adhesive material for use in residue confirmation include sharp edges and complicated shapes.

The object after cleaning is left at rest on a clean table in the darkroom. Thereafter, the object is irradiated with ultraviolet light by using an ultraviolet lamp (S13). Then, when the fluorescent paint applied to the chips is excited and its energy level returns to the ground state, it emits fluorescence as visible light. Although the object itself reflects ultraviolet light, the ultraviolet light is invisible, and therefore only the adhesive material for use in residue confirmation formed by coating the chips with fluorescent paint appears in the darkroom. Thus, the adhesive material for use in residue confirmation remaining on the object can be easily found.

Subsequently, the position of the found adhesive material for use in residue confirmation is marked on the object with an oil pen or the like (S14). This is because, while the adhesive material for confirming resides which is the colored chips needs to be observed under indoor light for the observation and photographical recording of its size, it is difficult to recognize under indoor light the area where the adhesive material for use in residue confirmation remains.

Subsequently, the size of the adhesive material for use in residue confirmation which is the colored chips remaining on the object is directly observed under indoor light (S15). In this step, the shape and size of the adhesive material for use in residue confirmation remaining on the object can be directly observed and measured. It is therefore possible to find which area of the object the chips remain in and what kind of chips remain.

It should be noted that, in place of observation under indoor light, the chips may be temporarily irradiated with white light in a darkroom and observed in that place. This alternative method allows alternately switching between the observation with the chips in an excited state in a darkroom and the normal observation with the chips in a ground state. This provides the advantage that the adhesive material for use in residue confirmation is easily found and observed.

It should be noted that observation in a darkroom or under indoor light is not necessarily required.

If no further observation under indoor light is required and this step (S15) is eliminated, the marking step (S14) is unnecessary. Furthermore, if the observation in a darkroom is unnecessary, such as the case where the chips are colored in an attention-getting color, the step (S13) of performing ultraviolet irradiation in the darkroom and the marking step (S14) are unnecessary.

It should be also noted that the above-described method for confirming the residue may be executed by an apparatus for residue confirmation. The apparatus for residue confirmation is composed of an ultraviolet irradiation device and an imaging device. The ultraviolet irradiation device performs the ultraviolet irradiation step (S13). The imaging device performs the direct observation step (S15) by imaging the object to be cleaned after cleaning.

Figure 3A:
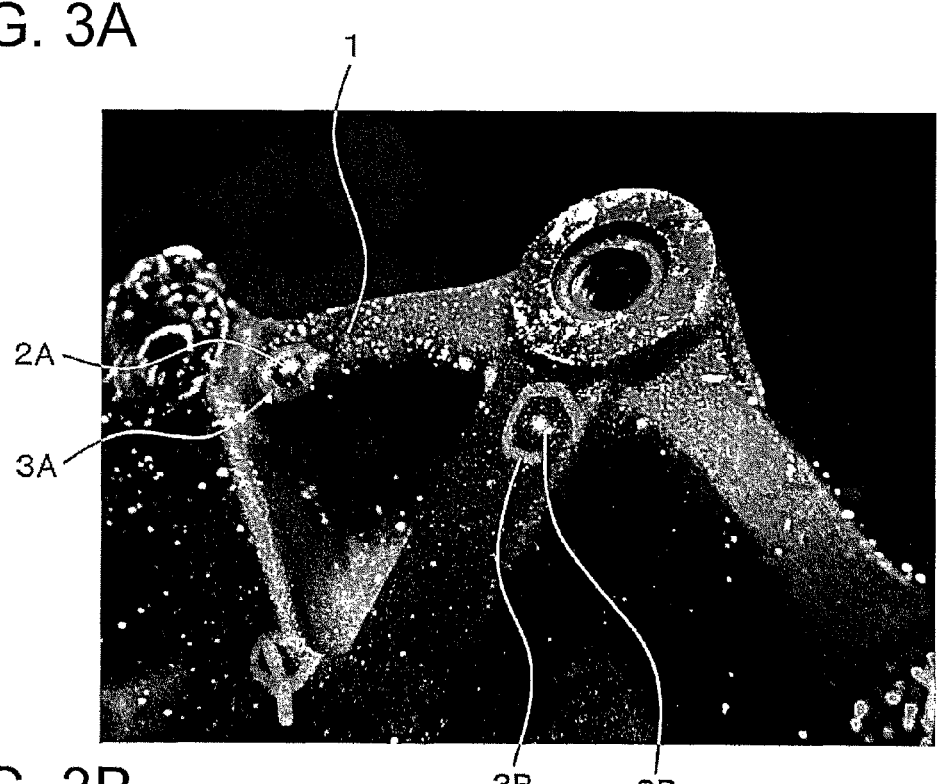
Figure 3B:
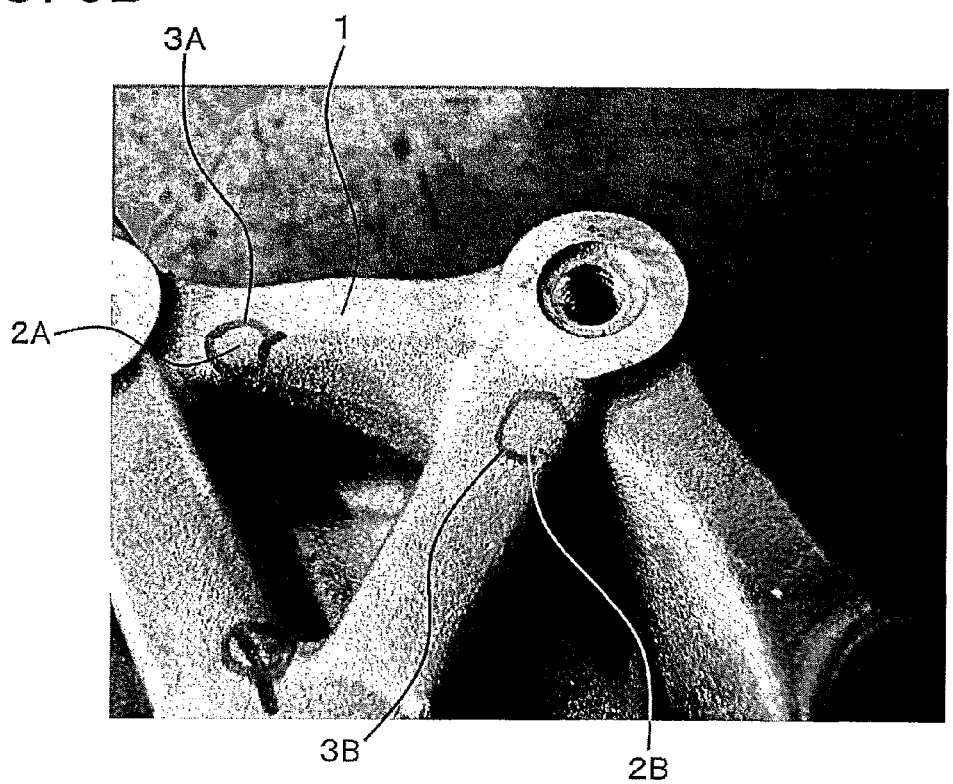

FIGS. 3A and 3B are photographs, substituted for the drawings, showing the state of the object after cleaning the object with the adhesive material for use in residue confirmation applied thereto, the adhesive material being formed by coating and coloring chips with fluorescent paint, wherein FIG. 3A is a photograph, substituted for the drawing, of the object after cleaning, taken under ultraviolet light in a darkroom, and FIG. 3B is a photograph, substituted for the drawing, of the same portion of the same object as FIG. 3A, taken under indoor light.

As shown in FIG. 3A, adhesive materials for use in residue confirmation, which are the chips colored with fluorescent paint, are observed to appear very clearly on an object 1 to be cleaned. Here, with the object 1 irradiated with ultraviolet light, markings 3A and 3B are applied with an oil pen so as to surround the positions where adhesive materials 2A and 2B of 0.2 mm or more are found.

Furthermore, as shown in FIG. 3B, the object 1 is observed without ultraviolet irradiation under indoor room. In this state, even if the positions with the markings 3A and 3B on the object 1 are visually observed, the adhesive materials 2A and 2B cannot be found. It should be noted that although in FIG. 3B, the same positions as those in FIG. 3A are shown by reference markings 3A and 3B, the adhesive materials 2A and 2B in those positions are actually invisible to the naked eye.

Figure 4A:
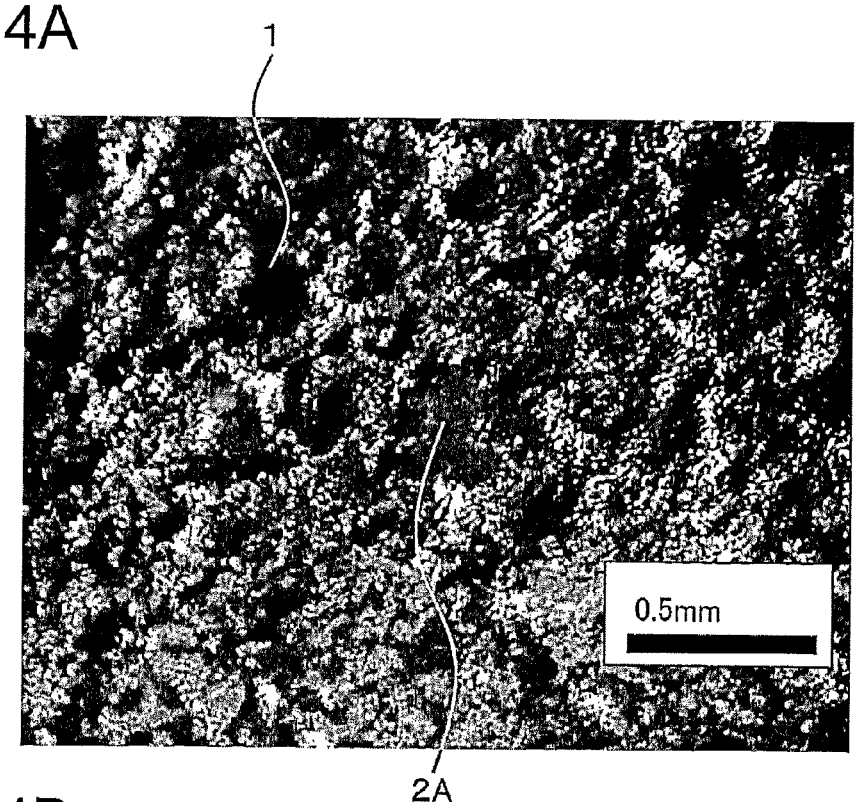
FIG. 4A is a magnified photograph, substituted for the drawing, of the position with a marking on the left side in FIG. 3B.
Figure 4B:
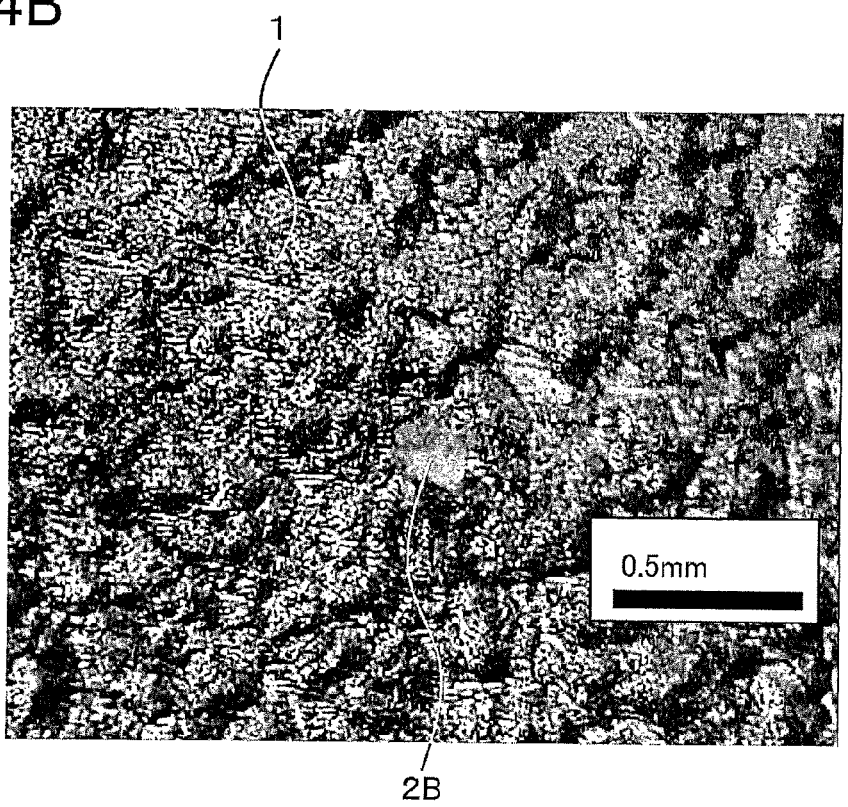
FIG. 4B is a magnified photograph, substituted for the drawing, of the position with a marking on the right side in FIG. 3B.

FIG. 4A is a magnified photograph, substituted for the drawing, of the position with the marking 3A on the left side in FIG. 3B, and FIG. 4B is a magnified photograph, substituted for the drawing, of the position with the marking 3B on the right side in FIG. 3B. In FIGS. 4A and 4B, the adhesive materials for confirmation of residues which remain in the positions with the markings 3A and 3B on the object 1 (see FIG. 3B) were observed with a graduated magnifying glass and photographed, each of the adhesive materials having a long side of about 0.3 mm.

In the related art method in which cleaning liquid used for cleaning an object to be cleaned is filtered by a filter to thereby obtain and evaluate a residue adhering to the object, although chips remaining on the object after cleaning can be separately observed, it is impossible to observe the object itself after cleaning or observe which area of the object the chips remain in and what kind of chips remain. In particular, it has been very difficult to find the residue of a chip whose area in plan view is 4 $mm^2$ or less, and it is normally impossible to find a chip having a long side of 1 mm or less (see FIG. 3B).

By using the colored chips as the adhesive material for use in residue confirmation, the present invention allows observation of the object itself after cleaning and direct observation of the adhesive material remaining on the surface of the object. Especially by using the chips colored with the paint, which emits visible light in an excited state, as the adhesive material for use in residue confirmation to confirm the adhesive material in an excited state, the chips can be highly effectively found (see FIG. 3A). This facilitates an improvement in the degree to which a water jet hits the area where chips remain, in a high-pressure cleaning machine.

In particular, the present invention is the first successful case to observe the chips having a long side of 1 mm or less in a state where they adhere to the object after cleaning.

It should be noted that although in the above-described example, the chips are colored with the fluorescent paint including a water-soluble fluorescent dye, the coloring method may be changed. Furthermore, although the description has been made by using the high-pressure cleaning machine as a cleaning machine to be subjected to the cleaning capacity evaluation, the present invention is not limited thereto, but can be used for cleaning capacity evaluations of various cleaning machines, such as soaking type cleaning machines, water-jet cleaning machines, oscillating cleaning machines, or spray low-pressure cleaning machines.

What is claimed is:

1. A method for confirmation of a residue remaining on an object to be cleaned after cleaning, comprising the steps of:

forming chips by cutting a workpiece;
    obtaining an adhesive material by coloring the chips with paint, the paint emitting visible light in an excited state;
    applying the adhesive material to the object to be cleaned,
    cleaning the object with the adhesive material applied thereto; and
    energizing the object after cleaning for excitation.

2. The method according to claim 1, wherein the chips are colored in a plurality of colors according to sizes of the chips.

3. The method according to claim 1, wherein the chips are made of a material of the same kind as that of the object.

4. The method according to claim 1, wherein the formation of the chips comprises extracting the chips from a process line in which the cutting of the workpiece is performed under conditions equivalent to those of a main cutting work to be applied to the object before cleaning.

* * * * *